(12) United States Patent
Rees

(10) Patent No.: US 6,555,386 B1
(45) Date of Patent: Apr. 29, 2003

(54) APPARATUS FOR COLLECTING A LIQUID SAMPLE

(75) Inventor: John Rees, Llandudno (GB)

(73) Assignee: Clinical Diagnostic Chemicals Limited, Glan Conwy (GB)

( * ) Notice: Subject to any disclaimer, the term of this patent is extended or adjusted under 35 U.S.C. 154(b) by 283 days.

(21) Appl. No.: 09/620,040

(22) Filed: Jul. 20, 2000

(30) Foreign Application Priority Data

Jul. 23, 1999 (GB) .............................................. 9917325

(51) Int. Cl.⁷ ................................................ G01N 1/10
(52) U.S. Cl. ........................ 436/180; 436/164; 436/165; 422/55; 422/58; 422/61; 422/99; 422/102; 422/947
(58) Field of Search .............................. 422/55, 57, 58, 422/61, 99, 102, 940, 946, 947; 436/164, 165, 180; 600/573, 580, 581

(56) References Cited

U.S. PATENT DOCUMENTS

| | | | | |
|---|---|---|---|---|
| 3,814,522 A | * | 6/1974 | Clark et al. .................. 356/246 |
| 3,898,982 A | * | 8/1975 | Katsuda ....................... 422/100 |
| 4,007,639 A | * | 2/1977 | Haeckel ....................... 422/931 |
| 4,248,830 A | * | 2/1981 | Kallies et al. ............... 422/100 |
| 4,314,570 A | | 2/1982 | Sarstedt |
| 4,397,318 A | * | 8/1983 | Burns .......................... 600/576 |
| 4,447,546 A | | 5/1984 | Hirschfeld |
| 4,528,187 A | * | 7/1985 | Truglio ........................ 356/246 |
| 4,634,679 A | * | 1/1987 | Horres, Jr. ................... 436/174 |
| 4,707,337 A | * | 11/1987 | Jeffs et al. .................. 422/100 |
| 4,769,025 A | * | 9/1988 | Sarstedt et al. ............. 422/916 |
| 4,784,834 A | | 11/1988 | Hirschmann |
| 4,981,654 A | * | 1/1991 | Kuntz et al. ................. 422/100 |
| 5,030,421 A | * | 7/1991 | Muller ......................... 356/244 |
| 5,230,864 A | * | 7/1993 | Columbus .................... 422/100 |
| 5,259,956 A | * | 11/1993 | Mercer et al. ............... 210/453 |
| 5,583,432 A | * | 12/1996 | Barnes ......................... 324/204 |
| 6,156,824 A | * | 12/2000 | Yamada et al. .............. 427/127 |
| 6,266,139 B1 | * | 7/2001 | Mannhardt ................... 356/244 |

FOREIGN PATENT DOCUMENTS

| | | |
|---|---|---|
| EP | 0 005 979 | 5/1978 |
| EP | 0 082 263 | 10/1982 |
| EP | 0483 117 A2 | 7/1986 |
| EP | 0 266 155 | 10/1986 |
| EP | 0 517 121 A2 | 5/1992 |
| GB | 1081819 | 3/1965 |

* cited by examiner

*Primary Examiner*—Maureen M. Wallenhorst
(74) *Attorney, Agent, or Firm*—Oppedahl & Larson LLP

(57) ABSTRACT

The apparatus for collection of a liquid sample (such as a sample of body fluid) includes a tube with a hollow bore extending longitudinally between a first open end and a second open end. The second end is longitudinally spaced from the first open end and the first end has a capillary opening for uptake of the liquid sample by capillary action. The capillary opening has a first axis and a second axis substantially perpendicular thereto. The first axis has a length greater than the internal diameter of the bore, and the second axis has a length less than the internal diameter of the bore. In use the capillary opening is contacted with the liquid sample to be collected. The liquid sample is taken up by capillary action into the bore without introduction of air into the bore.

28 Claims, 3 Drawing Sheets

APPARATUS FOR COLLECTING A LIQUID SAMPLE

BACKGROUND OF THE INVENTION

The present invention relates to apparatus for collecting a liquid sample, and in particular apparatus for collecting a sample of body fluid, for use in diagnosis.

Currently available apparatus used to collect small quantities of a liquid sample, such as a drop of blood from a finger prick, generally comprises a capillary tube of liquid-impervious material (such as plastic or glass), having a longitudinally extending hollow bore which is open at both ends. The internal diameter of the bore is typically approximately 0.1 to 3 mm and the length of the bore is typically about 50 mm. Such capillary tubes can take up liquid samples by capillary action. The sample is collected until the sample reaches a desired level in the bore (such as that indicated by markings or calibrations on the tube), or until the bore is completely filled, thus giving a known volume of sample. The liquid sample is subsequently transferred to an absorbent medium by contact of one of the open ends of the tubes with such an absorbent medium, for analysis.

One of the main problems with currently available capillary tubes is undesired entry of air into the bore if the uptake of liquid is deliberately or accidentally interrupted. This can cause an air lock in the bore, which hinders accurate collection of a predetermined volume of sample, and may lead to the collected sample flowing back down the tube and then dripping from the bottom end thereof. Furthermore, when collecting a sample of blood from a finger prick, it might be necessary to place the capillary tube down and squeeze out an extra drop of blood. It would be an advantage, therefore, if the uptake of a liquid sample by a capillary tube could be interrupted without the associated problems caused by entry of air into the bore.

OBJECTS OF THE INVENTION

It is an object of the present invention to provide an improved apparatus for collection of a liquid sample, which alleviates the problems associated with the prior art.

It is another object of the present invention to provide a method for analyzing a liquid sample using an improved capillary tube.

It is a further object of the present invention to provide a diagnostic kit for analyzing a liquid sample, again including an improved capillary tube.

SUMMARY OF THE INVENTION

The present invention provides apparatus for collection of a liquid sample, the apparatus comprising a tube having a hollow bore extending longitudinally between a first open end and a second open end, the second end being longitudinally spaced from the first end. The first end comprises a capillary opening for uptake of the liquid sample by capillary action, the capillary opening having a first axis and a second axis substantially perpendicular thereto. The first axis has a length greater than the internal diameter of the bore, and the second axis has a length less than the internal diameter of the bore.

The capillary opening is typically narrower than the internal diameter of the bore. This advantageously reduces the risk of entry of air into the bore when uptake of the sample is deliberately or accidentally interrupted. The likelihood of an airlock occurring in the bore may thus be minimized according to the invention.

The capillary opening may be provided by a flattened substantially rectangular pinched end of the tube. A tube with a flattened substantially rectangular pinched end is generally relatively cheap and easy to manufacture.

It is a preferred feature of the invention that the capillary opening has at least one side of greater length than the remaining sides. The side of greater length generally provides a flat sided extension which typically aids collection of a liquid sample. For example, it may be easier to apply a drop of blood from a finger prick to a flat sided extension than to a narrow opening of a tube.

The side of greater length preferably has at least one longitudinal groove which extends into the capillary opening. The grooves desirably draw the liquid sample from the point of collection towards the capillary opening of the bore.

In one embodiment of the present invention, the capillary opening includes a plurality of channels. Each of the plurality of channels preferably extends substantially along the capillary opening; more preferably they extend into the bore of the tube. The channels may be non-enclosed grooves, which typically channel the liquid sample into the bore, or alternately each channel may be a separate enclosed tubular conduit.

The amount of liquid sample a capillary tube can be charged with according to the invention depends on various factors, including the physical chemistry of the sample, the material used to make the tube, and the angle of contact of the capillary opening with the sample.

The aforementioned plurality of channels may advantageously enable faster charging of the liquid sample as each channel provides an independent capillary action.

It is a preferred feature of the present invention that at least part of the tube is optically transparent, enabling viewing of the collected liquid sample. The tube may be made of suitable extrudable plastics, such as polyethylene, polypropylene, or the like.

In a further embodiment, the tube has at least one calibration, such that an accurate volume of liquid sample can be collected. The bore may also be of predetermined length and internal diameter, such that when the bore is filled with liquid sample, a known volume is contained within the bore.

In a further embodiment of the present invention, the apparatus includes an outer barrel arranged to substantially surround and receive the tube. The outer barrel is typically hand holdable to aid collection of the liquid sample. The outer barrel is preferably provided with at least one transparent window such that at least part of the contents of the tube can be viewed. It may be appropriate to have at least one calibration on the transparent window, or for the window to be positioned such that at least one calibration on the tube can be viewed through the window.

It may sometimes be desirable to include at least one preservative for the liquid sample, the preservative being arranged to be received in the bore. For example the internal surface of the bore may be coated with a suitable chemical which prevents deterioration of the liquid sample through microbial contamination or clotting.

The present invention further provides a method for analyzing a liquid sample, which method comprises the following steps:

providing at least one tube having a hollow bore extending longitudinally between a first open end and a second open end, the second end being longitudinally spaced from the first end, the first end comprising a capillary opening, the capillary opening having a first axis and a second axis substantially perpendicular thereto, the first axis having a length greater than the internal diameter of the bore, and the second axis having a length less than the internal diameter of the bore;

(1) contacting the capillary opening with the liquid sample, such that the sample is taken up into the tube by capillary action;

(2) transferring the collected sample to a receiving member; and (3) analyzing the sample on the receiving member. Suitable liquid samples for analysis include blood, tears, urine, saliva, sweat, intestinal secretions, and the like.

The receiving member, mentioned in step (c) above, may comprise an absorbent material. The liquid sample may be transferred to the absorbent material by contact between the absorbent material and at least one of the first and second open ends of the tube. The second open end of the tube may be arranged to be permanently in contact with the absorbent material.

Furthermore it is sometimes desirable to collect a predetermined volume of the liquid sample which may then be transferred to the receiving member.

The sample may be analyzed using any of a number of methods known in the art, for example by an immunoassay or enzyme linked immunosorbent assay (ELISA). Alternately, the receiving member may be a microscope slide, and the sample may be analyzed using a microscope. The sample on the microscope slide may be stained using a differential stain, for example a gram stain, to typically stain target prokaryotic or eukaryotic cells. Alternately, a microscope may be used to count the number of specific cells present in a set volume of liquid sample transferred to a microscope slide.

The tube may be of any suitable longitudinal shape, such as arcuate or otherwise curved along the length, or it may have a substantially linear axis. A curved tube may advantageously enable collection of the liquid sample at the first open end of the tube with simultaneous dispensing of the sample from the second open end of the tube. The sample may be dispensed from the second open end directly onto the receiving member.

The present invention further provides a diagnostic kit for analyzing a liquid sample, which comprises at least one apparatus as described above and a reagent for reacting with a predetermined component of the liquid sample. For example, a diagnostic kit may include a reagent to test the presence of allergen specific IgE in a drop of blood.

The diagnostic kit preferably further includes a receiving member for receiving the liquid sample from the apparatus. The receiving member may be as hereinbefore described. At least one preservative for the liquid sample is preferably included in the diagnostic kit. The preservative may be as described above.

BRIEF DESCRIPTION OF THE DRAWINGS

For a fuller understanding of the invention, preferred embodiments are described below with reference to the accompanying drawings which are by way of example only. In the drawings.

DETAILED DESCRIPTION OF THE INVENTION

Figure 1:
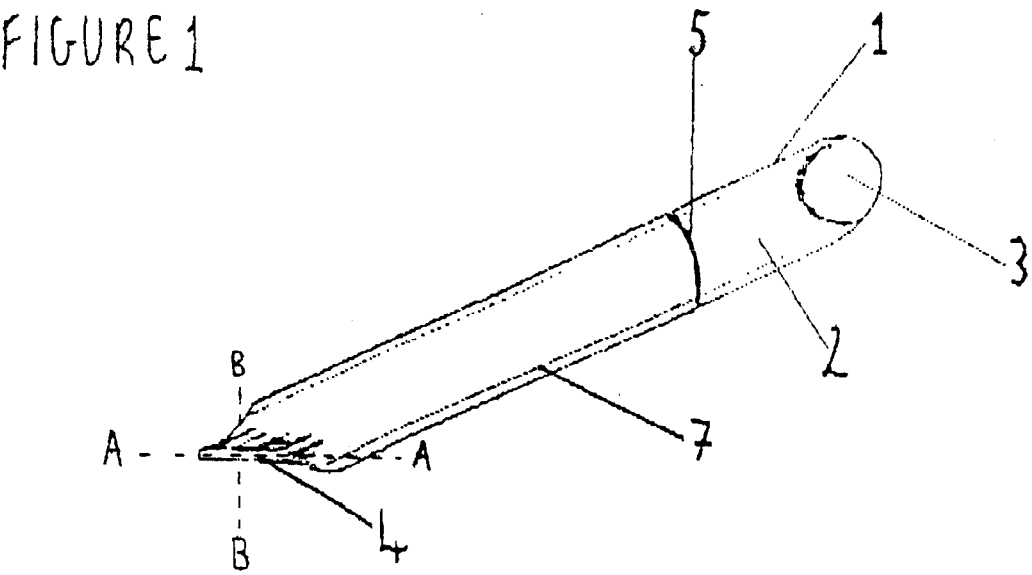
FIG. 1 shows an apparatus for collection of a liquid sample, comprising a tube with a capillary opening.

FIG. 1 illustrates an optically transparent tube (1) having a hollow bore (2) extending longitudinally between a circular opening (3) (of the same internal diameter as the bore (2)) and a flattened rectangular capillary opening (4). The length of the first axis of the capillary opening (denoted A—A) is greater than the internal diameter of the bore (2), and the length of the second axis of the capillary opening (denoted B—B) is less than the internal diameter of the bore (2). The flattened rectangular capillary opening (4) is formed by pinching the end of the tube (1).

When the apparatus is used for collection of a liquid sample, the capillary opening (4) is contacted with the liquid sample to be collected. The liquid sample is taken up into the bore (2) by capillary action until the bore (2) is charged to a calibrated level (5) indicated on the tube (1) or until the bore (2) is completely full. The internal surface (7) of the bore (2) may be coated with at least one preservative, for example, using a suitable chemical which prevents deterioration of the collected sample as a result of microbial contamination or clotting or the like.

Figure 2:
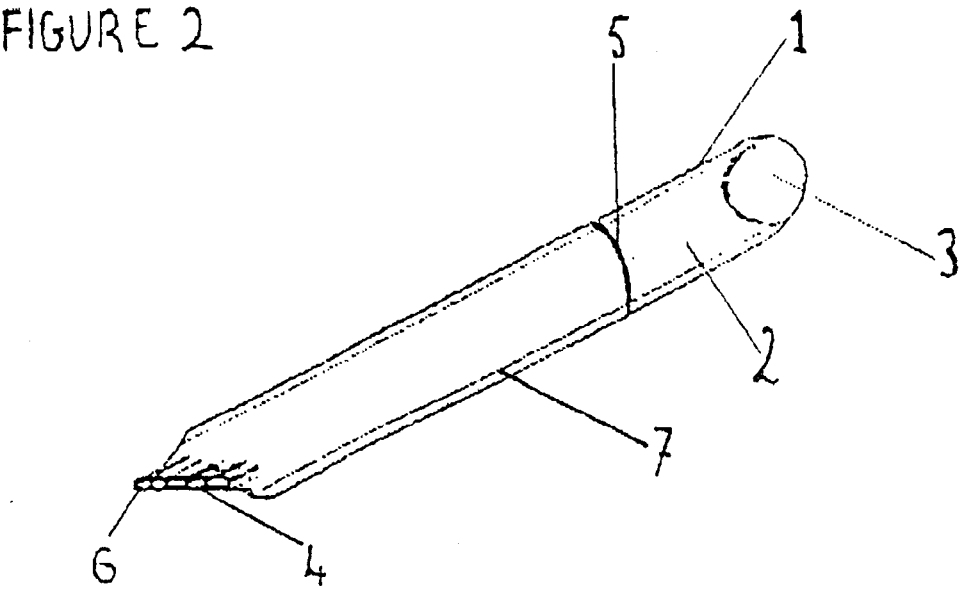
FIG. 2 shows a further embodiment of the apparatus of FIG. 1 where the capillary opening is provided by a plurality of channels.

The capillary opening (4) in the embodiment of FIG. 2 is provided by a plurality of channels (6). Each of the channels (6) is a separate conduit which extends along the capillary opening (4) and into the bore (2). Alternately the channels (6) may be formed by grooves (not shown) along at least one of the internal surfaces of the capillary opening.

Figure 3:
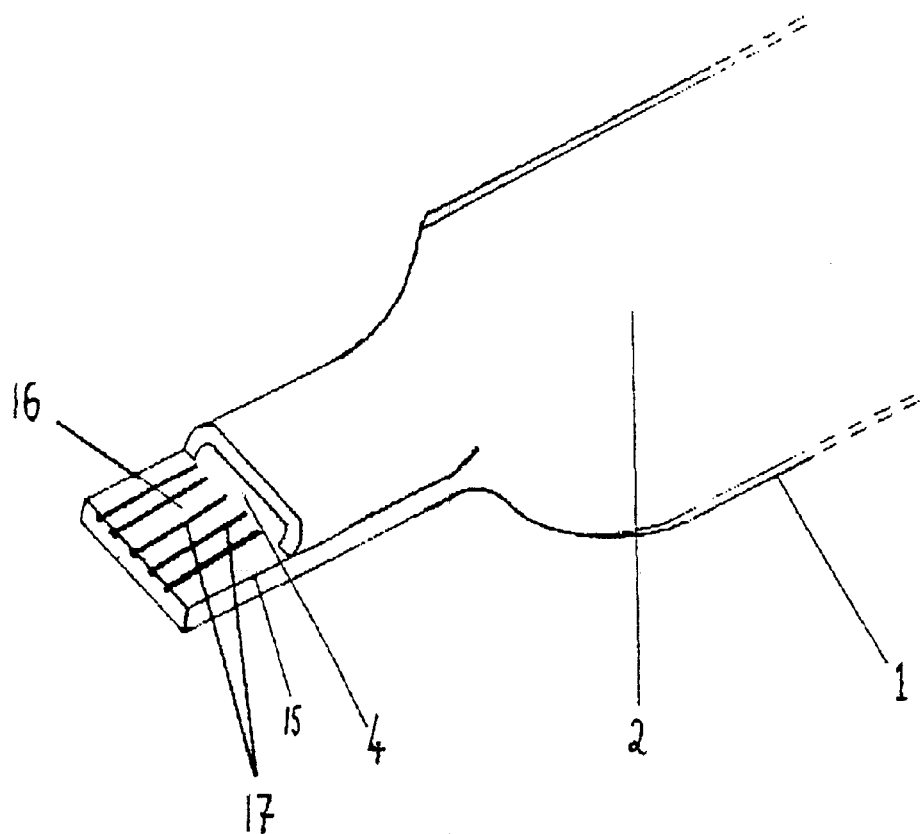
FIG. 3 shows the apparatus of FIG. 1 with a one-sided extension to the capillary opening.

FIG. 3 illustrates an adaptation of the capillary opening (4) of the apparatus of FIG. 1; like parts are denoted like reference numerals in FIGS. 3 and 1. The flattened rectangular capillary opening (4) has one side of greater length (15) than that of the remaining sides of the rectangle, providing a flat sided extension (16). The flat sided extension (16) has a plurality of longitudinal grooves (17) which extend into the capillary opening (4).

In use, the liquid sample to be collected is applied to the flat sided extension (16). The sample is drawn towards the capillary opening (4) along the longitudinal grooves (17) and is taken up into the bore (2).

Figure 4:
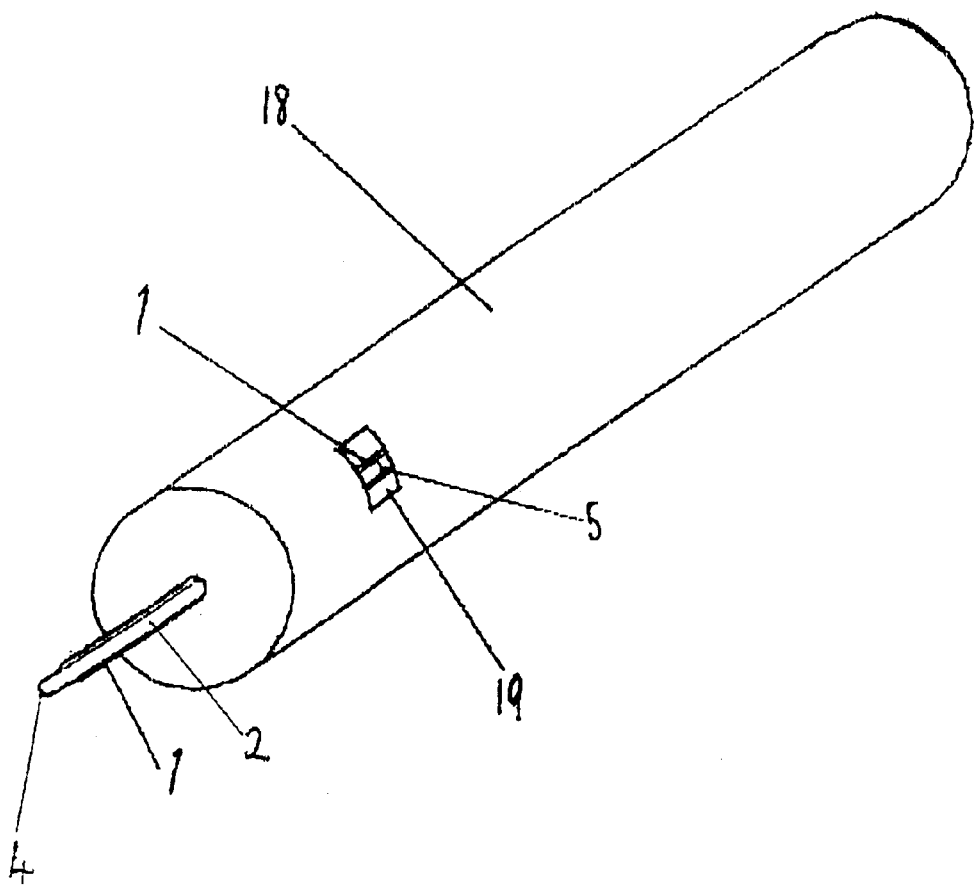
FIG. 4 shows a further embodiment of the present invention where the tube is provided within an outer barrel.

FIG. 4 illustrates a hand holdable outer barrel (18) which surrounds a tube (1) having a hollow bore (2) as depicted in FIGS. 1 to 3. The outer barrel (18) is provided with a transparent window (19) through which part of the contents of the tube (1) can be viewed. A calibrated level (5) indicated on the tube (1) can be seen through the transparent window (19). The capillary opening (4) is not encased by the outer barrel (18).

The apparatus of FIG. 4 can be used in a similar way to the apparatus illustrated in FIGS. 1 to 3, namely by contacting the capillary opening (4) with the liquid sample to be collected. The collected sample may then be transferred to an absorbent medium and subsequently analyzed.

What is claimed is:

1. Apparatus for collection of a liquid sample, said apparatus comprising a tube having a hollow bore extending longitudinally between a first open end and a second open end, said second end being longitudinally spaced from said first end, said first end comprising a capillary opening for uptake of said liquid sample by capillary action, said capillary opening having a first axis and a second axis substantially perpendicular thereto, said first axis having a length greater than an internal diameter of said bore, and said second axis having a length less than said internal diameter of said bore.

2. Apparatus according to claim 1, wherein said capillary opening is provided by a flattened substantially rectangular pinched end of said tube.

3. Apparatus according to claim 1, wherein said capillary opening has at least one side of greater length than that of the remaining sides.

4. Apparatus according to claim 3, wherein said at least one side of greater length has at least one longitudinal groove which extends into said capillary opening.

5. Apparatus according to claim 1, wherein said capillary opening is provided by a plurality of channels, each of said plurality of channels extending substantially along said capillary opening.

6. Apparatus according to claim 5, wherein said channels extend into said bore.

7. Apparatus according to claim 1, wherein at least part of said tube is optically transparent.

8. Apparatus according to claim 1, wherein said tube has at least one calibration mark thereon to indicate a predetermined volume of collected liquid sample therein.

9. Apparatus according to claim 1, further including an outer barrel arranged to substantially surround and receive said tube.

10. Apparatus according to claim 9, wherein said barrel has at least one transparent window such that at least part of contents of said tube can be viewed.

11. Apparatus according to claim 10, wherein said at least one transparent window has at least one calibration mark thereon to indicate a predetermined volume of collected liquid sample in said tube.

12. Apparatus according to claim 1, wherein an inner surface of said tube has at least one preservative for said liquid sample coated thereon.

13. A method for analyzing a liquid sample, which method comprises the following steps:

(a) providing at least one tube having a hollow bore extending longitudinally between a first open end and a second open end, said second end being longitudinally spaced from said first end, said first end comprising a capillary opening, said capillary opening having a first axis and a second axis substantially perpendicular thereto, said first axis having a length greater than an internal diameter of said bore, and said second axis having a length less than said internal diameter of said bore;

(b) contacting said capillary opening with said liquid sample, such that said sample is taken up into said tube by capillary action;

(c) transferring said collected sample to a receiving member; and (d) analyzing said sample on said receiving member.

14. A method according to claim 13, wherein said receiving member in step (c) comprises an absorbent material, said liquid sample being transferred by contact between said absorbent material and at least one of said first and second open ends of said tube.

15. A method according to claim 13, wherein a predetermined volume of said liquid sample is collected and transferred to said receiving member.

16. A diagnostic kit for analyzing a liquid sample, which kit comprises:

(a) apparatus for collection of a liquid sample, said apparatus comprising a tube having a hollow bore extending longitudinally between a first open end and a second open end, said second end being longitudinally spaced from said first end, said first end comprising a capillary opening for uptake of said liquid sample by capillary action, said capillary opening having a first axis and a second axis substantially perpendicular thereto, said first axis having a length greater than an internal diameter of said bore, and said second axis having a length less than said internal diameter of said bore; and (b) a reagent for reacting with a predetermined component of said liquid sample.

17. A diagnostic kit according to claim 16, further including a receiving member for receiving said liquid sample from said apparatus.

18. A diagnostic kit according to claim 16, wherein said capillary opening of said apparatus is provided by a flattened substantially rectangular pinched end of said tube.

19. A diagnostic kit according to claim 16, wherein said capillary opening of said apparatus has at least one side of greater length than that of the remaining sides.

20. A diagnostic kit according to claim 19, wherein said at least one side of greater length has at least one longitudinal groove which extends into said capillary opening.

21. A diagnostic kit according to claim 16, wherein said capillary opening of said apparatus is provided by a plurality of channels, each of said plurality of channels extending substantially along said capillary opening.

22. A diagnostic kit according to claim 21, wherein said channels extend into said bore.

23. A diagnostic kit according to claim 16, wherein at least part of said tube of said apparatus is optically transparent.

24. A diagnostic kit according to claim 16, wherein said tube of said apparatus has at least one calibration mark thereon to indicate a predetermined volume of collected liquid sample therein.

25. A diagnostic kit according to claim 16, wherein said apparatus further includes an outer barrel arranged to substantially surround and receive said tube.

26. A diagnostic kit according to claim 25, wherein said barrel has at least one transparent window such that at least part of contents of said tube can be viewed.

27. A diagnostic kit according to claim 26, wherein said at least one transparent window of said barrel has at least one calibration mark thereon to indicate a predetermined volume of collected liquid sample in said tube.

28. A diagnostic kit according to claim 16, wherein said apparatus has at least one preservative for said liquid sample coated on an inner surface of said tube.

* * * * *